Aug. 2, 1949. R. G. JELLY Plant Pat. 858
ROSE PLANT
Filed Aug. 25, 1947
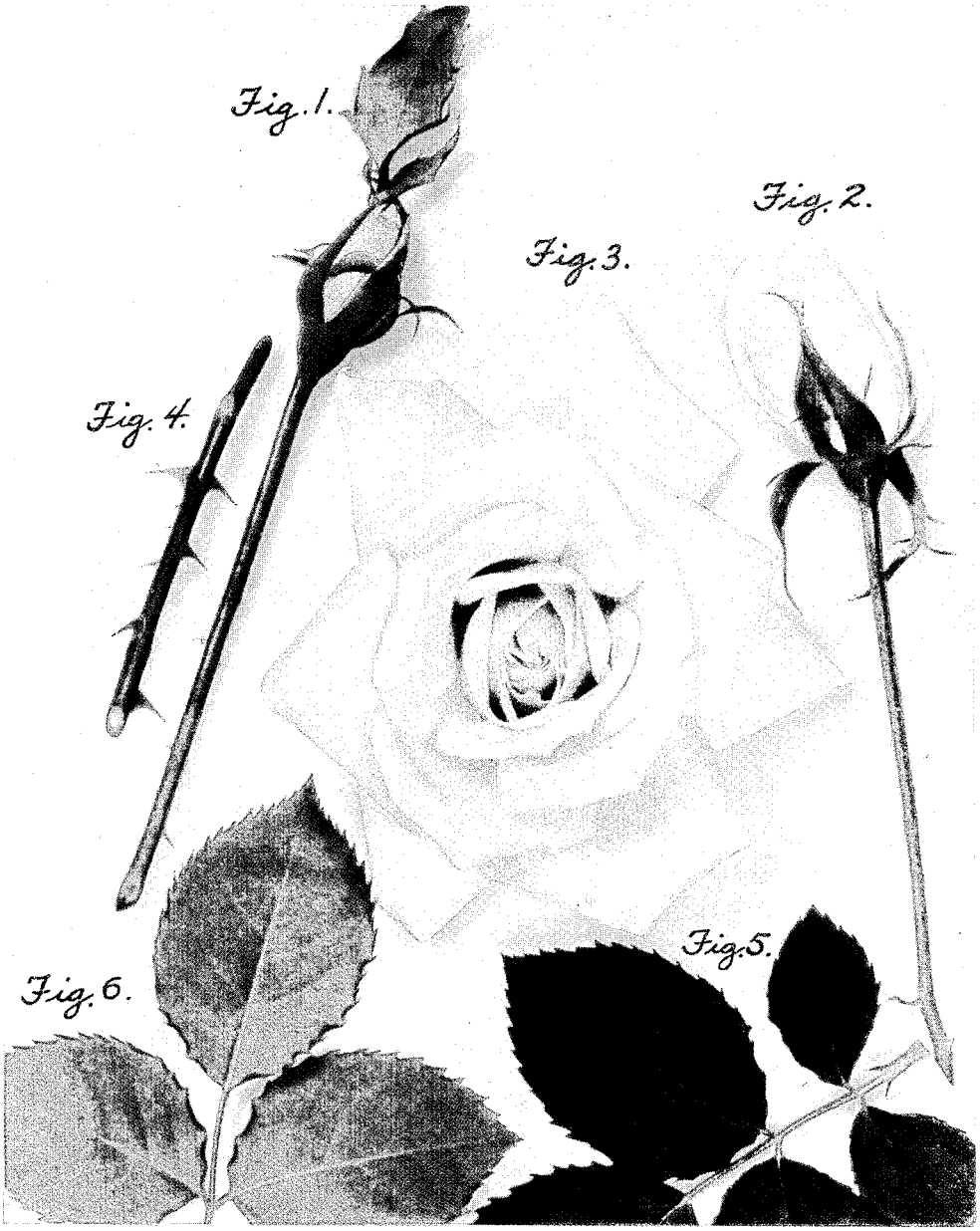
Inventor:
R. G. Jelly
By: Robb & Robb
Attorneys.

Patented Aug. 2, 1949

Plant Pat. 858

UNITED STATES PATENT OFFICE

858

ROSE PLANT

Robert G. Jelly, Richmond, Ind., assignor to The E. G. Hill Company, Richmond, Ind., a corporation of Indiana Application August 25, 1947, Serial No. 770,421

1 Claim. (Cl. 47—61)

The present invention relates to a new and distinct variety of rose plant, resulting from the cross of two well known varieties, hereinafter identified, and characterized as to novelty by its habits, the form, and coloring of the flower at different stages and the combination of certain characteristics derived from both of its parents.

To be more specific, this new rose is distinct from any others known to commerce by the long-pointed shape of the bud in the early stages, opening into a high centered half-open flower of pleasing pink color and form. It may also be said at this point that one of its most unusual features is that the mature flower is deeper in color than the semi-mature flower. It is resistant to mildew and blackspot and is moderately free in habit.

It will be apparent to one acquainted with the parents of this new variety, that it inherited its size of flower, good foliage and resistance to disease from its seed parent, and color and habit of growth from its pollen parent "Countess Vandal." This combination and mutation of traits has, therefore, produced a greatly improved and satisfactory rose plant unknown to commerce at this time.

In the drawing are illustrated:

Fig. 1, a specimen of the bud before the calyx breaks;

Fig. 2, a specimen of the flower as first petal opens;

Fig. 3, a specimen of full-open flower (the size in all instances being reduced to about one-half of normal);

Fig. 4 shows a section of the stem, showing form and color and arrangement of the thorns; and Figs. 5 and 6 show specimens of foliage upper and lower surfaces thereof, respectively.

The following is a more detailed description of this new variety, color terminology being in accordance with Ridgway's Color Standard; except where otherwise indicated by ordinary dictionary definitions:

Type: Bush; greenhouse; for cut flowers.
Classification: Hybrid tea.
Breeding: Seedling.
*Seed parent.*—"H. M. S. Queen Mary" (Plant Patent No. 249).
*Pollen parent.*—"Countess Vandal" (Plant Patent No. 38).

Propagation: Holds its distinguishing characteristics through succeeding propagations by cuttings, grafting and budding.

*Flower*

Locality where grown: Richmond, Indiana.
Flowers borne: Singly, on medium long stems.
Quantity of bloom: Moderate in greenhouse.
Continuity: Continuous.
Fragrance: Slight.
Bud:
*Peduncle.*—Medium long; medium heavy; erect; stiff; medium green; medium rough; numerous yellow prickles.
*Before calyx breaks.*—*Size*—medium. *Form*—long; ovoid; with slender, much cut foliaceous parts extending beyond the tip of the bud equal to one-half or more of its length.
*As calyx breaks.*—*Color*—Begonia Rose, Plate I.
*As first petal opens.*—*Size*—medium. *Form*—pointed; ovoid. *Color*—outside: Geranium Pink, Plate I; inside: Chrome Yellow base, Plate III, shaded to Mikado Orange along veins, Plate III; upper part of petal Hermosa Pink, Plate I.
*Opening.*—Opens up well.
Bloom: Size, when fully open—large; 6 inches to 7 inches.
*Petalage.*—Very double; from 60 to 65 petals; arranged regularly.
*Form.*—Very high centered at first; remaining high centered; petals at first very loosely rolled outward, and retaining this form later at maturity.
Petals: No particular sheen or velvety texture.
*Shape.*—Outside—obovate; with apex flat or with slight point. Intermediate—obovate; with apex flat. Inside—obovate; with apex slightly pointed.

This description of a newly opened flower was made from a rose grown in a greenhouse at Richmond, Indiana, in the month of July, 1947:

*Color.*—*Outside petal*—outside surface: Deep Rose Pink, Plate XII; inside surface: Hermosa Pink, Plate I. *Intermediate petal*—outside surface: Begonia Rose, Plate I; Inside surface: Geranium Pink, Plate I. *Inner petal*—outside surface: Rose Doree, Plate I; inside surface: Tyrian Rose, Plate XII.

This description was made from a rose that was open for three days in a greenhouse at Richmond, Indiana, in the month of July, 1947:

*Color.—Outside petal*—outside surface: Rose Pink, Plate XII; inside surface: Hermosa Pink, Plate I. *Inside petal*—outside surface: Begonia Rose, Plate I; Inside surface: Eosine Pink, Plate I.

*General color effect.*—Newly opened full-blown flower—Deep Rose Pink, Plate XII, on outer petals, shaded to Begonia Rose, Plate I, at heart of half-open bud. Three days open—Eosine Pink, Plate I, at center shaded to Hermosa Pink, Plate I, on outside petals. Chrome Yellow, Plate III, still evident at base of outside petals.

*Behavior.*—Drop off cleanly; fading light pink.

*Flower longevity.*—Six days in July kept at living room temperatures.

*Reproductive organs*

Stamens: Medium to many; arranged regularly about pistils.

Filaments: Medium long; yellow; most with anthers.

Anthers: Medium large; yellow to reddish; all open at once.

Pollen: Very sparse; yellow.

Pistils: Medium in number.

Styles: Uneven; short to medium; thin; bunched; reddish color.

Stigma: Yellow.

Ovaries: All enclosed in calyx.

Hips: Globular with inconspicuous neck; Russet; moderately smooth; walls thick and fleshy. *Color*—Deep Orange.

Sepals: Falling soon; very long. *Color*—Inside—Light Paris Green, Plate XVIII; outside—Mineral Green, Plate XVIII.

Seed: Many; large.

*Plant*

Foliage:

Leaves.—Compound of 3, 5, and 7 leaflets; normally abundant; medium size; moderately heavy.

Leaflets.—Shape—ovoid; with apex acute. Base—acute. Margin—simple serrate.

Color.—*Mature*—upper surface: normal green; under surface: gray-green. *Young*—upper surface: moderately red; under surface: red.

*Rachis (the supporting stem of the compound leaf).*—Medium. Upper side—grooved. Under side—sparsely thorny.

*Stipules.*—Moderately short; narrow; curved downward from rachis; moderately short points carried forward and upward.

*Disease.*—Resistant to mildew and blackspot.

Growth:

*Habit.*—Upright, little branched.

*Growth.*—Moderately free.

*Canes.*—Moderately heavy.

*Main stem.*—Bright green.

*Thorns.*—Several; long; hooked downward; with long narrow base.

*Prickles.*—Few; green-bronze.

*Branches.*—Bright green. *Thorns*—several; long; hooked downward; with long narrow base. *Prickles*—few; green-bronze.

*New shoots.*—Bronze. *Thorns*—several; long; hooked downward; with long narrow base. *Prickles*—few; green-bronze.

I claim:

A new and distinct variety of rose plant, characterized as to novelty by the shape of its flower bud and development thereof into half-open flower at maturity; coloring of the bud and flower, and resistance to disease; and free habit, substantially as shown and described.

ROBERT G. JELLY.

No references cited.